United States Patent
Rogers

(10) Patent No.: US 9,801,529 B2
(45) Date of Patent: Oct. 31, 2017

(54) ROTATION OF OUTRIGGER DURING MEDICAL PROCEDURE

(71) Applicant: Intuitive Surgical Operations, Inc., Sunnyvale, CA (US)

(72) Inventor: Theodore W. Rogers, Alameda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/947,039

(22) Filed: Nov. 20, 2015

(65) Prior Publication Data

US 2016/0073864 A1 Mar. 17, 2016

Related U.S. Application Data

(62) Division of application No. 14/254,515, filed on Apr. 16, 2014, now abandoned, which is a division of application No. 12/080,172, filed on Mar. 31, 2008, now Pat. No. 8,727,966.

(51) Int. Cl.
*A61B 1/00* (2006.01)
*A61B 1/018* (2006.01)
*A61B 1/05* (2006.01)
*A61B 17/29* (2006.01)

(52) U.S. Cl.
CPC .......... *A61B 1/018* (2013.01); *A61B 1/00098* (2013.01); *A61B 1/05* (2013.01); *A61B 17/29* (2013.01); *A61B 2017/2906* (2013.01)

(58) Field of Classification Search
USPC ........................ 600/104–107, 114
See application file for complete search history.

(56) References Cited

U.S. PATENT DOCUMENTS

| | | |
|---|---|---|
| 3,689,104 A | 9/1972 | Phillip |
| 5,166,787 A | 11/1992 | Irion |
| 5,782,752 A | 7/1998 | Lichtman et al. |
| 5,808,665 A | 9/1998 | Green |
| 5,895,350 A | 4/1999 | Hori |
| 5,899,850 A | 5/1999 | Ouchi |
| 5,984,932 A | 11/1999 | Yoon |
| 6,352,503 B1 | 3/2002 | Matsui et al. |
| 6,761,685 B2 | 7/2004 | Adams et al. |
| 6,817,974 B2 | 11/2004 | Cooper et al. |
| 6,986,738 B2 | 1/2006 | Glukhovsky et al. |
| 7,029,435 B2 | 4/2006 | Nakao |
| 7,918,845 B2 | 4/2011 | Saadat et al. |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Matthew J Kasztejna

(57) ABSTRACT

A medical device such as an endoscope, a laparoscope, or other device including an entry guide uses outriggers or arms that are mounted on the distal end of the entry guide and rotationally deployed to provide separation of instruments when the entry guide reaches a work site. Deployment can be implemented with as few as one cable or actuator to operate the arms. This mechanism may achieve working separation in a short axial length without complicating instrument channels that may be used for other instruments introduced through the entry guide.

15 Claims, 3 Drawing Sheets

(56) References Cited

U.S. PATENT DOCUMENTS

| | | |
|---|---|---|
| 8,727,966 B2 | 5/2014 | Rogers |
| 2005/0038317 A1 | 2/2005 | Ratnakar |
| 2005/0096502 A1 | 5/2005 | Khalili |
| 2007/0167680 A1 | 7/2007 | Miyamoto et al. |
| 2007/0299387 A1 | 12/2007 | Williams et al. |
| 2008/0065105 A1 | 3/2008 | Larkin et al. |
| 2008/0071289 A1* | 3/2008 | Cooper .............. A61B 1/00087 606/130 |
| 2008/0269562 A1 | 10/2008 | Marescaux et al. |
| 2014/0228633 A1 | 8/2014 | Rogers |

* cited by examiner

ROTATION OF OUTRIGGER DURING MEDICAL PROCEDURE

BACKGROUND

Minimally invasive medical procedures allow diagnostic tests and corrective surgeries with a minimal amount of damage to healthy tissues. For example, laparoscopic surgery, which is minimally invasive surgery on the abdomen, generally introduces surgical instruments through small incisions. The inserted instruments are typically rigid, have small diameters, and end with effectors that can be manually or robotically controlled to perform a desired medical procedure on a work site. Laparoscopic surgery typically uses two or more incisions to provide separation between the instruments and to allow insertion of the instruments from different directions for triangulation on the work site inside the body. The separation and triangulation of instruments is often critical to allowing the instruments to work cooperatively during surgical manipulations.

Endoscopes are also known that are sufficiently flexible to be inserted via a natural orifice and to follow a natural lumen such as the digestive tract to a work site. Medical instruments can then be inserted through such an endoscope to reach the work site. In particular, a multi-channel endoscope can act as a flexible conduit for simultaneous insertion of multiple diagnostic or surgical instruments, but the flexibility of these endoscopes have limited the controllable degrees of freedom of the instruments at the work site. For example, a flexible endoscopic system may only provide control of roll, insertion/extraction, and sometimes grip. Further, the instruments inserted through an endoscope must be sufficiently flexible to follow channels provided in the endoscope and typically run parallel to the centerline of the endoscope. As a result, flexible endoscopic instruments generally have minimal separation from one another and little or no triangulation relative to each other. This makes basic surgical manipulations such as suturing difficult, if not impossible to accomplish with conventional flexible endoscopic equipment.

Medical systems have been proposed that attempt to provide separation and triangulation of instruments delivered through a flexible endoscope. U.S. Pat. No. 7,029,435 to Nakao, for example, describes an endoscope having a distal end that is longitudinally split into segments that can be made to separate after the endoscope reaches a work site. U.S. Pat. No. 6,761,685 to Adams et al. and U.S. Pat. No. 6,352,503 to Matsui et al. describe endoscopes having instrument lumens at the perimeter of the endoscope cross-section so that the separation of inserted instruments is about equal to the diameter of the endoscope, and further separation or triangulation of the instruments can be achieved by deflecting the instruments or the lumens that guide the instruments. However, most current approaches to providing separation and triangulation of instruments in a flexible endoscope require a relatively long length to create a relatively small separation, and the instruments generally lack solid support and have little or no useful triangulation.

In view of the current state of minimally invasive medical equipment and procedures, it would be desirable to have simple devices and procedures for achieving useful triangulation and working separation between instruments at the distal end of a rigid or flexible endoscope. Ideally, the device would be such that device failures occur only in a safe manner that permits withdrawal of the device.

SUMMARY

In accordance with an aspect of the invention, a mechanism, which may be implemented as an addition to a flexible or rigid entry guide, uses outriggers or arms that are mounted on the distal end of the entry guide and rotationally deployed at a work site to provide separation and triangulation for medical instruments associated with the arms. Deployment of the arms can be implemented with as few as one cable or actuator. This mechanism may achieve working separation in a shorter axial length than other systems and without complicating instrument channels that may be used for other instruments introduced through the entry guide.

In one embodiment of the invention, a medical device for a minimally invasive procedure includes an entry guide, an outrigger, and a pivot structure rotatably attaching an end of the outrigger to the entry guide. A fixture such as a guide tube or a mounting for a medical instrument is at an end of the outrigger opposite to the end where the pivot structure attaches the outrigger to the entry guide. The pivot structure permits rotation of the outrigger from a retracted position that provides a small cross-section for insertion or removal of the device to a deployed position that provides maximal separation of the fixture from a center line of the entry guide. Further, the structure of the fixture can be tailored to bias an instrument at an angle toward or away from the center line of the entry guide to enhance triangulation with or separation from other instruments.

Another embodiment of the invention is a medical device including an entry guide with two outriggers attached to a distal end of the entry guide. Each outrigger is rotatably mounted and has a fixture for an associated medical instrument. The mounting permits rotation of the outriggers from retracted positions to deployed positions. With the outriggers in the retracted position, the medical device has a smaller cross-section, which can be as small as the entry guide. The deployed positions of the outriggers provide greater separation of the fixtures and the associated medical instruments than is provided in the retracted positions.

BRIEF DESCRIPTION OF THE DRAWINGS

Use of the same reference symbols in different figures indicates similar or identical items.

DETAILED DESCRIPTION

Figure 1A:
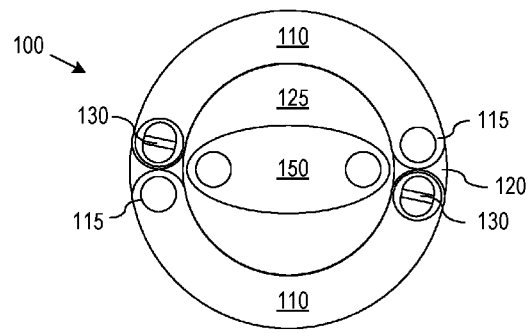
FIG. 1A shows the distal end of a medical device in accordance with an embodiment of the invention having rotationally deployable arms that are in retracted positions.
Figure 1B:
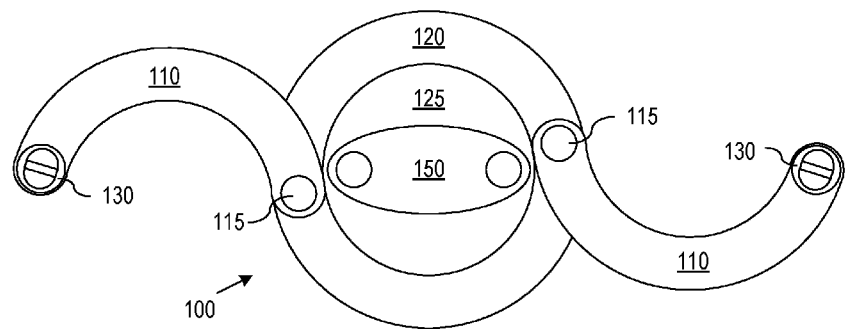
FIG. 1B shows the distal end of the device of FIG. 1A when the arms are deployed.

In accordance with an aspect of the invention, the working separation of medical instruments at the distal end of an endoscope or other minimally invasive medical device can be increased using rotationally deployable arms or outriggers. FIGS. 1A and 1B show end views of one such medical device 100 in accordance with an exemplary embodiment of the invention. Device 100 has two outriggers 110 that can be retracted or folded in as shown in FIG. 1A or deployed as shown in FIG. 1B. Outriggers 110 when retracted provide a small area cross-section for insertion or removal of device 100 through a small incision or a natural orifice. FIG. 1A particularly shows an embodiment where outriggers 110 when retracted fit within the cross-section of an entry guide 120. Alternatively, outriggers 110 when in the retracted positions could extend somewhat beyond the cross-section of entry guide 120 and still be suitable for insertion and removal for a minimally invasive medical procedure.

Each outrigger 110 has a pivot or hinge 115 that rotatably attaches the outrigger 110 to entry guide 120, and hinges 115 have respective rotation axes located away from a centerline of entry guide 120. The rotation axes may in general be at an acute angle, e.g., 0° to about 30°, relative to the center line. During a medical procedure, when the end of device 110 nears a work site, outriggers 110 can be rotated from their retracted positions as shown in FIG. 1A to their deployed positions as shown in FIG. 1B. In the deployed positions as shown in FIG. 1B, instruments 130 that are mounted on or pass through guides or lumens in outriggers 110 have a separation much greater than (i.e., about three times) the diameter of entry guide 120 of device 100. The separation of instruments 130 as thus provided by outriggers 110 is a vast improvement over the separation abilities of tools that are confined to run parallel and adjacent in a conventional entry guide. Additionally, fixtures such as mountings or guide tubes for instruments 130 can be oriented in or on outriggers 110 to provide instruments 130 with an inward bias for triangulation of or outward bias for additional separation of instruments 130.

Figure 1C:
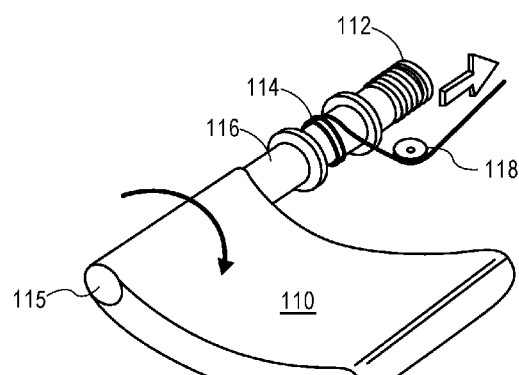
FIG. 1C illustrates an actuation mechanism for a rotationally deployed arm in accordance with an embodiment of the invention.

Actuation or deployment of outriggers 110 requires rotating both outriggers 110 by approximately 180 degrees from their retracted positions. FIG. 1C illustrates one mechanism for outrigger actuation. In the illustrated embodiment, each outrigger 110 has a torsion spring 112 attached to a hinge pin 116 of the hinge 115 of the outrigger 110. Spring 112 can be loaded to keep the outrigger 110 in the retracted position as in the illustrated embodiment or alternatively in the deployed position. A cable 114 is wrapped around a hinge pin 116 and extends around a guide pulley or rounded surface 118 back through the entry guide on which outrigger 110 is mounted. With cable 114 wrapped as shown, pulling on cable 114 causes cable 114 to unwind from hinge pin 116 and outrigger 110 to rotate in a direction opposite to the torque applied by spring 112, e.g., toward its deployed position in the illustrated embodiment. Releasing tension in cable 114 allows spring 112 to rotate outrigger 110 back to the retracted position. Sensors (not shown) such as hall sensors, optical thru-beam or reflective sensors, or other suitable sensors may be provided to detect whether outriggers 110 are retracted and/or deployed and to send signals to a control mechanism (not shown) attached to cable 114.

Many alternative actuation mechanisms could be employed for outriggers 110. For example, torsion spring 112 could be replaced with a second cable that is wrapped around hinge pin 116 in the opposite direction from the wrapping of cable 114, so that pulling on one cable deploys outrigger 110 and pulling on the other cable retracts outrigger 110. Outrigger 110 could alternatively be deployed or retracted by an actuator (not shown) such as a linear or rotary shape memory alloy actuator, a small electric motor, a piezoelectric actuator, or any kind of actuator that may be located at the distal end of entry guide 120 and remotely activated. Further, outriggers 110 could be coupled together so that deployment or retraction of one outrigger 110 causes the other rigger 110 to deploy or retract, and with outriggers 110 coupled together, a single cable or actuator can be used to operate both outriggers 110.

The axes of hinges 115 for outriggers 110 may be parallel to or at an angle with respect to the centerline of entry guide 120. When pivots 115 are angled, the angle can direct the tips of instruments 130 either toward one another or away from each other as outriggers 110 are deployed. The choice of whether an inward or outward angle is desired will depend on the characteristics of the specific instrument 130. For instance, outriggers 110 can position instruments 120 with a 30° total inward toeing to achieve a significant level of triangulation even with straight shafted instruments. Alternatively, an outward angle could help to increase the separation of instruments 130.

Entry guide 120 may be rigid or flexible in alternative embodiments of the invention. In an embodiment in which device 100 is rigid, which is common for a laparoscope, entry guide 120 can be a tube of rigid material such as stainless steel, titanium, or composite materials such as carbon fiber or glass fiber material having an outside diameter of about 12 to 22 mm. In an embodiment in which device 100 is a flexible endoscope, entry guide 120 can be a flexible tube of similar dimensions. One architecture for a flexible endoscope uses vertebrae made of plastic or other suitable material enclosed in a jacket of neoprene or similar material. The walls of entry guide 120 may be about 1 to 6 mm thick and may include cable guides and cables or other structures used to control outriggers 110 and in some embodiments instruments 130.

Outriggers 110 have a cross-section approximately in the shape of a half ring in the illustrated embodiment of FIGS. 1A and 1B, and with two outriggers 110 being employed, each outrigger 110 may wrap nearly halfway around the cross section of entry guide 120. The advantage of the arc shape for outriggers 110 is that the length of outriggers 110 can be maximized without obstructing a lumen 125 in entry guide 120. An unobstructed lumen 125 can thus act as a guide for insertion of medical instruments or removal of tissue samples, regardless of whether outriggers 110 are in the retracted configuration of FIG. 1A or the deployed configuration of FIG. 1B. A camera 150 in a lumen 125 can thus provide an unobstructed viewing field even when outriggers 110 are retracted, for example, during insertion of entry guide 120 for a medical procedure. Outriggers 110 could alternatively have other shapes, including shapes that may obstruct lumen 125 when outriggers 110 are retracted if additional instruments are not required except when outriggers 110 are deployed.

FIGS. 1A and 1B illustrate the example of a camera 150 being in a lumen 125 of entry guide 120. More generally, any medical instrument with a small enough diameter and sufficient flexibility could be inserted through one or more lumens 125 in entry guide 120. Some examples of such medical instruments include but are not limited to cutting or grasping instruments, biopsy tools, fiber lasers for cutting and cauterizing, stapling instruments, and snares or bag instruments. The particular types and sizes of medical instruments will in general depend on the procedure being performed and the nature of entry guide 120. In particular, the instruments must be small enough to fit within an available lumen 125. If entry guide 120 has bends, for example, in embodiments where device 100 is a flexible endoscope that follows a natural lumen, the inserted instruments should be sufficiently flexible to follow the path of entry guide. Instruments with more rigid construction can be used when entry guide 120 is straight, for example, in embodiments where device 100 is a rigid laparoscope.

Instruments 130 may be fixed to respective outriggers 110 before insertion of entry guide 120 and only removable by removing the whole entry guide 120 from the patient, or each outrigger 110 may support the end of a flexible guide tube that forms the distal end of a lumen through which a full-length flexible instrument may be inserted or removed at any time during a procedure. Such guide tubes can be made of materials such as rubber, Teflon, polyethylene or other plastic, or a flexible metal tube. An advantage of having instruments 130 fixed on outriggers 130 is that instruments can have a diameter that is larger than the diameter of an instrument that could be inserted through a lumen in outrigger 110. Additionally, mounting instruments 130 on outriggers 110 leaves more space in entry guide 120 for additional medical instruments or permits device 100 to have a smaller diameter while delivering the required instruments to the work site of a medical procedure. However, use of a lumen running to the ends of outriggers 110 provides the ability to more easily change instruments 130 during a medical procedure.

Figure 2:
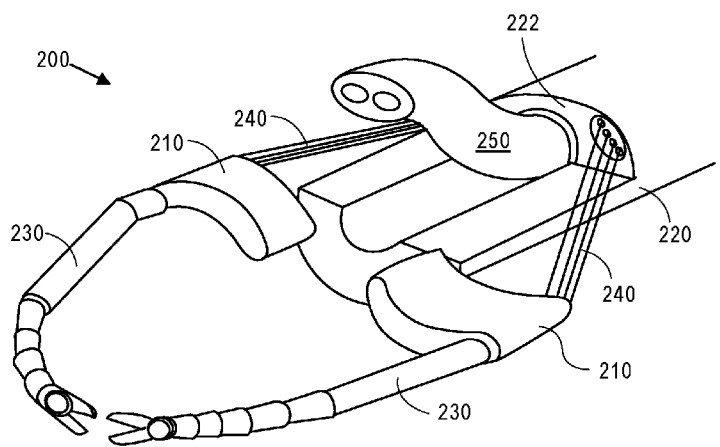
FIG. 2 shows a perspective view of the distal end of a medical device in accordance with an embodiment of the invention using cables for control of instruments attached to rotationally deployed arms.

FIG. 2 illustrates a medical device 200 having outriggers 210 attached to an entry guide 220 and instruments 230 that are fixed on outriggers 210. The outriggers 210 and entry guide 220 of FIG. 2 may be substantially the same as outriggers 110 and entry guide 120 described above with reference to FIGS. 1A and 1B. Each instrument 230 in the embodiment illustrated in FIG. 2 is a multi-jointed arm with grasping forceps as an end effector and can be remotely and/or robotically controlled using cables. Some embodiments of suitable instruments 230 are further described in U.S. Pat. No. 6,817,974 to Cooper et al., which is hereby incorporated by reference in its entirety.

FIG. 2 shows cables 240 used for control of instruments 230. With outriggers 210 deployed as illustrated in FIG. 2, one or more of cables 240, which extend along a length of entry guide 220, run diagonally outward from a surface 222 of entry guide 220 to the proximal side of each outrigger 210 and from there into the instrument 230 that is being controlled. Cables 240 thus run free across a gap in the illustrated embodiment, but alternatively could be housed collectively or individually in a flexible jacket. Device 200 could be operated to maintain tension in cables 240 while outriggers 210 are retracted, and spools or other mechanisms could let out additional cable length as outriggers 210 are being deployed. Keeping cables 240 taut when outriggers 210 are in the retracted positions may permit manipulation of instruments 230, for example, for steering entry guide 220 during insertion of device 200 along a natural lumen. Alternatively, cables 240 could be slack while outriggers 210 are retracted and only made taut when outriggers 210 are deployed for use of instruments 230 at a work site.

FIG. 2 also illustrates how a section of entry guide 220 can be cut out to provide free space for movement of cables 240 as outriggers 210 are deployed. Alternatively, control cables could pass through the hinges or pivot pins of outriggers 210 and through outriggers 210 to instruments 230. However, the cut out section for cables 240 also permits space for a camera 250 to be kept back from the ends of instruments 230 while a positioning mechanism for camera 250 provides separation for camera 250 in a direction substantially perpendicular to the separation of instruments 230 when outriggers 210 are deployed. Camera 250 may, for example, be a stereoscopic camera mounted on a jointed mechanism capable of lifting the end of camera 250 away from the central lumen of entry guide 220 while a wrist mechanism controls the direction that camera 250 points. A suitable camera system for this purpose is further described in U.S. Pat. App. Pub. No. 2008/0065105, entitled "Minimally Invasive Surgical System," which is hereby incorporated by reference in its entirety. The perpendicular separation of camera 250 can improve viewing of instruments 230 and the work site when performing a medical procedure. Camera 250 could alternatively be inserted further and directed to look down on the work site or otherwise provide any desired view to the operator of device 200.

Figure 3:
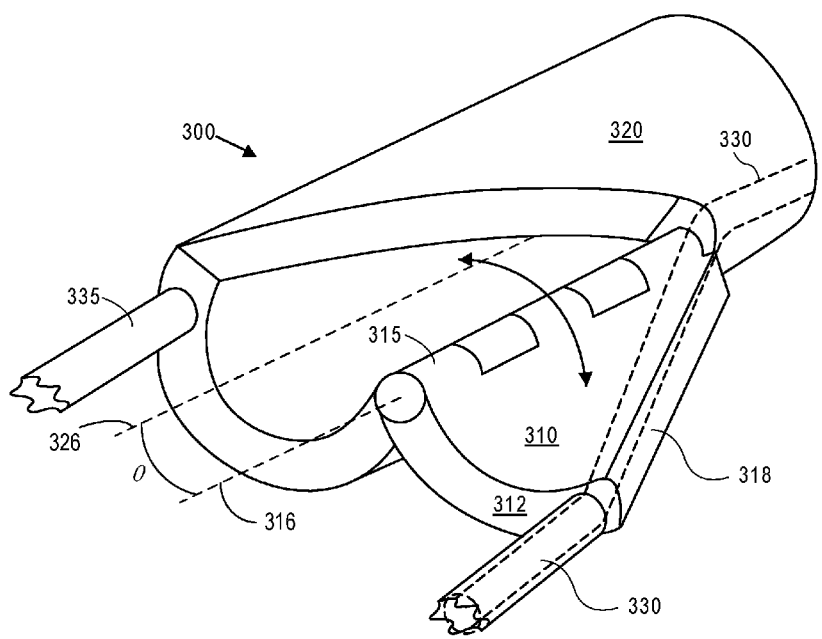
FIG. 3 shows a perspective view of the distal end of a medical device in accordance with an embodiment of the invention having arms that are shaped for safe removal in the event of a mechanical failure.

FIG. 3 illustrates a device 300 in accordance with an embodiment of the invention employing an outrigger 310 shaped to encourage passive retraction when an entry guide 320 is pulled backward through a body lumen or orifice. Outrigger 310 has a tapered shape and in the illustrated embodiment is approximately a triangular section of a cylinder. As shown, outrigger 310 has three sides, which are a front face 312 of outrigger 310 at the end of entry guide 320, a hinge 315 or pivot axis 316, and a surface 318 at an angle to hinge 315. Hinge 315 and surface 318 are preferably longer than front face 312 of each outrigger 310. In the illustrated embodiment, hinge 315 or pivot axis 316 is substantially parallel to entry guide 320, i.e., at an angle θ about equal to 0° with a centerline 326 of entry guide 320, and surface 318 corresponds to a diagonal cut through a portion of entry guide 320. Alternatively, hinge 315 and pivot axis 316 could be along the diagonal cut in entry guide 320. Outrigger 310 may be constructed of a flexible material to facilitate articulation and steering of entry guide 320 when outrigger 310 is retracted. Outrigger 310 could be made of a non-isotropic material that is stiff in a radial direction so that hinge 315 remains approximately straight during folding or unfolding of outrigger 310 but flexible in other directions to facilitate passive retraction. For example, outrigger 310 could contain metal leaves that are parallel to surface 312 and encased in rubber. In the case of a failure of the actuation mechanism (not shown) of outrigger 310 when outrigger 310 is deployed distal to a narrow body lumen or orifice, the action of retracting entry guide 320 would cause the narrow end of the triangular elements of outrigger 310 to engage the walls of the lumen or orifice, and the triangular element would then serve as a wedge to force outrigger 310 to collapse back into the retracted position as entry guide 320 is further withdrawn into the lumen.

FIG. 3 also illustrates an example in which the instrument fixture associated with outrigger 310 is a flexible guide tube 330 that runs through outrigger 310, hinge 315, and back through entry guide 320. With this configuration, rotation of outrigger 310 on hinge 315 can move the end of guide tube 330 from being within the diameter of entry guide 320 when outrigger 310 is in the retracted position to being almost a full diameter of the entry guide outside the diameter of entry guide 320 when outrigger 310 is in the deployed position. The opening in outrigger 310 through which guide tube 330 runs can have an end portion that directs an instrument at an angle relative to the axis of entry guide 320 when outrigger 310 is deployed. For example, two similar outriggers 310 can have guide tubes that guide instruments toward each other to achieve triangulation for instruments such as graspers working co-operatively at a work site.

When the instrument extending from outrigger 310 is removable, instrument control cables would typically pass through the body of the instrument. But some axes of motion of the instrument, such as roll or I/O (linear in/out) may be best actuated by a mechanism located in or on outrigger 310 or the body of entry guide 320 or guide tube 330 in which case the actuating cables for these manipulations of the instruments may be external to the instrument the same as in the case where the instruments are fixed on the outriggers. For example, an instrument may be inserted through and locked in guide tube 330, and guide tube 330 may be rotated for roll of the instrument.

FIG. 3 further illustrates that although two outriggers may be employed for maximum separation between instruments, a single outrigger 310 is also effective at increasing the separation of instruments. For example, an instrument inserted through the guide tube 330 in outrigger 310 is separated by about twice the diameter of guide tube 320 from an instrument inserted through a guide tube 335 in the wall of entry guide 320. In yet other embodiments of the invention, three or more rotationally deployed arms or outriggers can be provided to separate instruments in desired directions from an entry guide.

Figure 4:
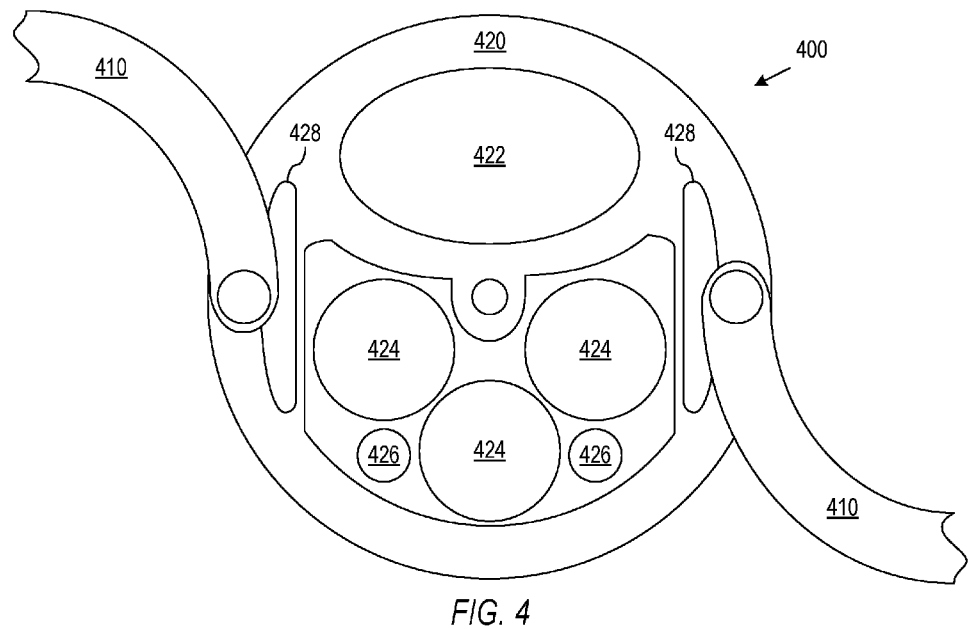
FIG. 4 shows a cross-section of a multi-channel entry guide in accordance with an embodiment of the invention.

FIG. 4 shows a cross-sectional view of a medical device 400 that provides outriggers 410 for wide separation of instruments and multiple channels within the cross-sectional area of an entry guide 420 for additional instruments and accessories. In an exemplary embodiment, entry guide 420 has a diameter of about 18 mm, and outriggers 410 can provide a separation of up to 45 mm or more between instruments (not shown) that are mounted on or run through outriggers 410. Within the body of entry guide 420 are a camera channel 422 that can accommodate a stereoscopic camera, three instrument channels 424 able to accommodate instruments up to 5 mm in diameter, two accessory channels 426 that can be about 2 mm in diameter for accessories such as ports for introduction of gases or solutions or for suction, and one or more lumens in each of regions 428 for control cables for operation of outriggers 410 and the instruments at the ends of outriggers 410. At the distal end of medical device 400, guides 422 and 424 can feed into a single large lumen or a half cylindrical cavity such as illustrated in FIG. 2.

Figure 5:
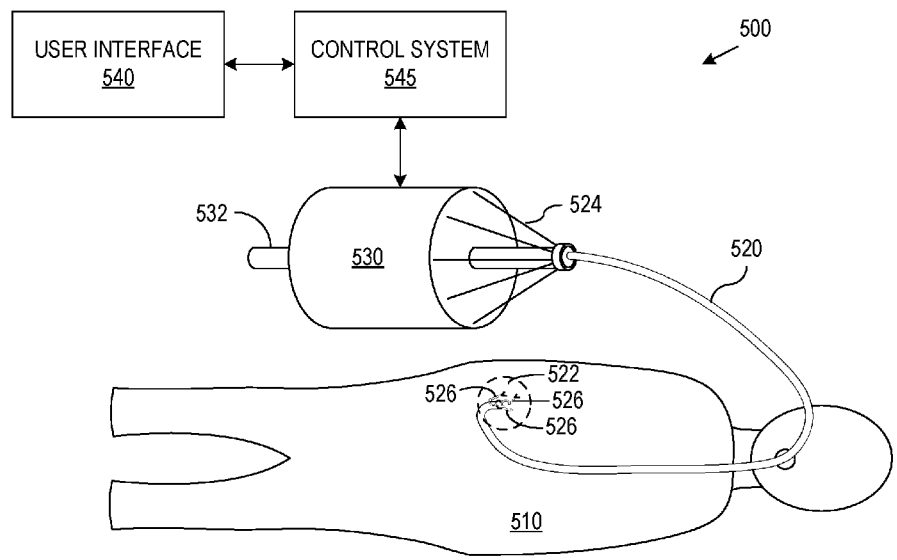
FIG. 5 illustrates an application of a flexible, robotically-controlled endoscope having rotationally deployed arms in accordance with an embodiment of the invention.

FIG. 5 illustrates a system 500 for performing a minimally invasive medical procedure on a patient 510. System 500 employs a flexible endoscope or entry guide 520 that can be inserted though a natural orifice such as the mouth of patient 510 and directed along a natural lumen such as the digestive tract of patient 510. Distal end 522 has outriggers that are deployed when distal end 522 of entry guide 520 is inside patient 510. The deployment can occur when distal end 522 of entry guide 520 reaches a work site in patient 510 or during the insertion process, for example, when making an incision in the wall of the natural lumen in order to facilitate access by device 520 of a work site outside the natural lumen. To minimize the size of the incision, the outriggers may be retracted after making an incision and before passing through the incision. The deployments provide separation between medical instruments 526 that are attached to or directed through the ends of the outriggers.

The medical instruments 526 on the outriggers and other medical instruments 526 that may be inserted through entry guide 520 can be used to perform surgery or other procedures on patient 510. Cables 524 for control of the medical instruments 526 and the position or shape of entry guide 520 run through entry guide 520 and connect to an actuator package 530 that contains actuators that control tension in cables 524 for operation of the device. An interface for sensor signals and video signals from entry guide 520 or the instruments 526 may be provided through actuator package 530, a control system 545, or a user interface 540. Electrical or other power and communication signals could also be sent to or received from actuators or control electronics at distal end 522. A user interface 540 provides an operator, e.g., a medical doctor, with a visual display such as stereoscopic (3-D) display and includes manipulator controls that the operator moves to operate the instruments 526 at distal end 522. A control system 545 converts movements of the manipulators in user interface 540 into control signals that cause actuator package 530 to apply tension to cables 524 as necessary to cause the desired movement of the instruments and entry guide 520. Some suitable user interfaces and control systems are further described in U.S. Pat. No. 5,808,665, entitled "Endoscopic Surgical Instrument and Method for Use," which is hereby incorporated by reference in its entirety.

Actuator package 530 additionally includes a port 532 to instrument lumens in entry guide 520. Alternatively, instrument lumens may exit the sides of entry guide 520 in front of actuator package 530. Instruments 526 can thus be inserted into and removed from entry guide 520 via port 532. The instruments 526 inserted through port 532 can be controlled through user interface 540, control system 545, and actuator package 530 or may have their own signal interfaces and actuator control systems.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A process comprising: inserting a length of a device into a patient until a distal end of the device reaches a work site inside the patient, wherein an outrigger that is rotatably mounted on the distal end is in a retracted position while the device is being inserted, the outrigger including a triangular section of the device, that is rotatable about a rotation axis along a first edge of the triangular section: rotating the outrigger about the rotation axis so that the outrigger deploys from the retracted position to a deployed position while the distal end is inside the patient, wherein the rotation axis is fixed at a first angle with a centerline along the length of the device, the first angle being less than 90°; inserting an instrument from a proximal end of the device, through a first lumen that runs through the outrigger, so that a portion of the instrument extends from an opening in the outrigger, the opening being at a first distance from the rotation axis; and performing a medical procedure at the work site using the portion of the instrument extending from the outrigger, wherein the medical procedure is performed while the outrigger is in the deployed position, and the opening is further from the centerline when the outrigger is in the deployed position than when the outrigger is in the retracted position.

2. The process of claim 1, wherein inserting the length of the device comprises causing the distal end of the device to follow a natural lumen inside the patient.

3. The process of claim 1, wherein in the retracted position the outrigger overlaps a cross-section of the distal end of the device.

4. The process of claim 3, further comprising employing a camera in the distal end during insertion of the device, wherein the triangular section of the outrigger is shaped to allow unobstructed viewing with the camera while the outrigger is in the retracted position.

5. The process of claim 1, wherein the first angle is zero.

6. The process of claim 1, wherein the first angle is non-zero.

7. The process of claim 1, further comprising:
rotating the outrigger from the deployed position back to the retracted position; and
removing the device from the patient while the outrigger is in the retracted position.

8. The process of claim 1, further comprising removing the device from the patient, wherein contact of a second edge of the triangular section of the outrigger with tissue of the patient pushes the outrigger from the deployed position to the retracted position.

9. The process of claim 1, wherein inserting the length of the device comprises:
inserting the distal end of the device along a natural lumen;
rotating the outrigger to the deployed position;
cutting an incision in a wall of the natural lumen with the device while the outrigger is in the deployed position;
rotating the outrigger to the retracted position; and
directing the distal of the device end through the incision while the outrigger is in the retracted position.

10. The process of claim 1, wherein:
the device comprises an entry guide and a hinge that attaches the outrigger to the entry guide and permits rotation of the entry guide about the rotation axis; and wherein
the process further comprises employing a camera in a second lumen of the entry guide for viewing during insertion of device while the outrigger is in the retracted position.

11. The process of claim 10, further comprising employing the camera in the second lumen of the entry guide for viewing while the outrigger is in the deployed position.

12. The process of claim 1, further comprising:
keeping a second outrigger that is rotatably mounted on the distal end in a second retracted position while the device is being inserted;
rotating a second outrigger about a second rotation axis so that the outrigger deploys to a second deployed position while the distal end is inside the patient, wherein the rotation axis is fixed at a second angle with the centerline; and
performing the medical procedure using a second instrument extending from the second outrigger.

13. The process of claim 12, further comprising employing a camera in a second lumen of the device for viewing while the outriggers are in the retracted positions.

14. The process of claim 13, further comprising employing the camera in the second lumen for viewing while the outriggers are in the deployed positions.

15. The process of claim 1, further comprising removing the device from the patient, wherein:
the device comprises an entry guide and a hinge that attaches the outrigger to the entry guide and permits rotation of the outrigger about the rotation axis;
the triangular section of the outrigger has a second edge at a non-zero angle with the hinge; and
contact of the second edge with tissue of the patient pushes the outrigger from the deployed position toward the retracted position while the device is being removed.

* * * * *